US008173440B2

(12) United States Patent  
Paolacci et al.

(10) Patent No.: US 8,173,440 B2
(45) Date of Patent: May 8, 2012

(54) NANOPOROUS MATERIAL FOR ALDEHYDES WITH DIRECT OPTICAL TRANSDUCTION

(75) Inventors: Hélène Paolacci, Paris (FR); Thu-Hoa Tran-Thi, St Fargeau-Ponthierry (FR)

(73) Assignees: Commisariat a l'Energie Atomique, Paris (FR); Centre National de la Recherche Scientifique-CNRS, Paris Cedex (FR)

( * ) Notice: Subject to any disclaimer, the term of this patent is extended or adjusted under 35 U.S.C. 154(b) by 0 days.

(21) Appl. No.: 12/066,616

(22) PCT Filed: Sep. 15, 2006

(86) PCT No.: PCT/FR2006/002124
§ 371 (c)(1),
(2), (4) Date: Mar. 12, 2008

(87) PCT Pub. No.: WO2007/031657
PCT Pub. Date: Mar. 22, 2007

(65) Prior Publication Data
US 2008/0220534 A1 Sep. 11, 2008

(30) Foreign Application Priority Data
Sep. 15, 2005 (FR) ...................... 05 09445

(51) Int. Cl.
*G01N 21/75* (2006.01)
(52) U.S. Cl. ........ 436/167; 436/128; 436/164; 436/166; 436/178; 422/82.05
(58) Field of Classification Search .................. None
See application file for complete search history.

(56) References Cited

U.S. PATENT DOCUMENTS 5,494,824 A * 2/1996 Tanaka et al. .............. 435/288.7
6,235,532 B1 5/2001 Uttamchandani et al.
6,500,921 B1 12/2002 Fuller et al.

FOREIGN PATENT DOCUMENTS
WO WO 2004/104573 12/2004

OTHER PUBLICATIONS

Kucheyev, S.O., et al., Atomic laer deposition of ZnO on ultralow-density nanoporous silica aerodel monoliths, 2005, Applied Physics Letters, vol. 86(8), pp. 83108. Feb. 18, 2005 online.*
Pinheiro, Heloisa L.C., et al. Spectrofluorimetric determination of formaldehyde in air after collection onto silica cartridges coated with Fluoral P, available online Jun. 2, 2004, Microchemical Journal, vol. 78, pp. 15-20.*
Ingersoll, et al., Using Sol-Gel-Based Platforms for Chemical Sensors, Chemtech, Washington, DC, US vol. 27, No. 1, Jan. 1997, pp. 26-31, XP002060846, ISSN: 0009-2703, pp. 26-28.

* cited by examiner

Primary Examiner — Yelena G Gakh
Assistant Examiner — Robert Xu
(74) Attorney, Agent, or Firm — Miller, Matthias & Hull LLP

(57) ABSTRACT

The invention concerns a method for detecting and/or assaying and/or capturing at least one aldehyde, preferably formaldehyde, including a step of contacting a gas stream with a material comprising a nonporous metal oxide sol-gel matrix, said matrix containing at least one probe molecule bearing at least one reactive function capable of reacting with at least one aldehyde function. The invention also concerns the material for implementing said method, a method for preparing same, and sensors incorporating such materials.

15 Claims, 11 Drawing Sheets

Acridine yellow

Dimethyl yellow

Pararosaniline 1-(2,4-dinitrophenyl)
hydrazine (DNPH)

1-methyl-1-
(2,4-dinitrophenyl)hydrazine

2-Hydrazinobenzothiazole 3-methyl-2-benzothiazolinone
hydrazone hydrochloride 5-(dimethylamino)naphthalene
-1-sulphonyl hydrazide Hydralazine or
1-Hydrazinophthalazine N-methyl-4-hydrazino
-7-nitrobenzofurazan

NANOPOROUS MATERIAL FOR ALDEHYDES WITH DIRECT OPTICAL TRANSDUCTION

CROSS-REFERENCE TO RELATED APPLICATION

This application is a U S National Stage Application of PCT Application No. PCT FR2006/002124, filed on Sep. 15, 2006, which claims priority under the Paris Convention to French Patent Application No. FR 05 09445, filed on Sep. 15, 2005

FIELD OF THE DISCLOSURE

The present invention relates to the field of the metrology of aldehydes, for example in contaminated environments, and also to the pollution control of said environments. The environment may be an exterior or interior (e.g. domestic) atmosphere, contaminated or uncontaminated by at least one aldehyde, preferably formaldehyde.

BACKGROUND OF THE DISCLOSURE

More particularly, it relates to a novel material capable of reacting with at least one gaseous aldehyde, preferably formaldehyde, and also to its sol-gel preparation method.

It also relates to a method for detecting and/or quantifying and/or trapping at least one gaseous aldehyde, especially formaldehyde, based on measurements of the variation of at least one physicochemical property of said material.

It lastly relates to the use of these novel materials in optical transduction sensors which can be exploited for a metrology of the aldehydes in an environment, and also to devices enabling pollution control.

The term "aldehyde" denotes any organic molecule having a terminal carbonyl functional group preferably chosen from formaldehyde, acetaldehyde, propionaldehyde, butryaldehyde, acrolein, pentanal, hexanal and benzaldehyde.

When the notion of pollution is raised, it is conventional to refer to the pollution of the air outside. Furthermore, most of the epidemiological surveys carried out to establish correlations between pollution and the appearance of respiratory diseases usually only involve pollutants measured outside of dwellings. However, most people spend most of their time indoors. The quality of the air inside therefore appears particularly important from the point of view of health and well-being.

It is only recently that studies have mentioned the possibility of the role of chemical pollutants of the environment indoors in the increase in the prevalence of respiratory diseases.

Aldehydes are among the most abundant domestic chemical pollutants. Their sources are extremely numerous. These sources may be, in particular, connected to an external production such as the photooxidation of methane. However, the main sources for the release of aldehydes are found inside dwellings and are very diverse:
  resins and adhesives used to manufacture chipboard, particle board and plywood;
  urea/formaldehyde insulating foams used as thermal insulation, by injection into walls and partitions; and
  in textile coverings, wallpaper, paints, leather, etc.

Formaldehyde is also a preservative, disinfectant and desiccant. For these reasons, it is widely used as a solvent in hospital surroundings for disinfecting surgical instruments and also in the funeral service industry where embalming is carried out.

Formaldehyde is the most studied of aldehydes as it is widely used in the manufacture of very many construction products and various equipment. The release of formaldehyde varies depending on the temperature and humidity conditions. Its pungent odor is detected by a person at low concentrations (from 0.048 to 0.176 ppm or from 0.06 to 0.22 $mg/m^3$). Exposure to formaldehyde causes irritation which is experienced by most of the population at concentrations between 1 and 3 ppm, this irritation being rapidly aggravated when the content rises. Most individuals cannot, in effect, tolerate a prolonged exposure at 4-5 ppm. At 10-20 ppm, signs of severe irritation of the ocular mucous membranes and airways occurs from the start of exposure. Staying, even briefly, in an atmosphere where the formaldehyde concentration is greater than 50 ppm may cause serious disorders of the respiratory system (acute pulmonary edema, tracheal and bronchial ulcers, etc.). Due to long-term risks, formaldehyde has been classified as carcinogenic by the International Agency for Research on Cancer.

Consequently, the French national legislation has developed so that it is now recommended not to exceed a formaldehyde content of 0.2 ppm, or 0.25 $mg/m^3$, in dwellings insulated using urea/formaldehyde foams. Furthermore, the World Health Organization (WHO) recommends that the formaldehyde concentration does not exceed 0.080 ppm, or 0.1 $mg/m^3$, for a 30-minute exposure, this value corresponding to an order of magnitude below that for which there is a risk of harm occurring.

Considering the harmful effects of such chemical pollutants on public health, it appears necessary to measure and control the contents of aldehydes, especially including formaldehyde, in contaminated environments, whether they be outside or inside, and to offer novel pollution-control devices.

The detection methods that are already commercially available are based on trapping aldehydes by reaction with a suitable molecule, then analyzing them by gas or liquid chromatography.

In certain methods, the aldehyde, especially including formaldehyde, is trapped on an absorber or a solid support (silica or octadecyl-grafted silica) impregnated with a reactant such as 2,4-dinitrophenylhydrazine (DNPH) or 2-hydroxymethylpiperidine, capable of reacting with the aldehyde to form a product, a hydrazone or an oxazolidine. For example, the NIOSH 2451 method consists of a take-up of formaldehyde on a solid absorbent impregnated with 2-hydroxymethylpiperidine, followed by a gas chromatography analysis. The detection limits of this method are from 0.01 to 38 ppmv.

Due to the non-specificity of these reactants for formaldehyde, the aforementioned methods only allow a detection of formaldehyde when the trapping step is coupled to a gas or liquid chromatography analysis which makes it possible to differentiate the various reaction products.

Nash was the first to identify a mixture of reactants capable of reacting specifically in solution with formaldehyde. These reactants are a β-diketone, for example acetylacetone and ammonium acetate. They give rise to the formation of a highly fluorescent derivative, 3,5-diacetyl-2,6-dihydrolutidine (DDL) [Nash T., Biochem. J., 55, 416, (1953)]. Sawicki et al. then extended this reaction to other ketones such as dimedone [Sawicki E. et al., Mikrochim. Acta, 148, (1968); Sawicki E. et al., Mikrochim. Acta, 602, (1968)]. In this case, the final product is 3,3,6,6-tetramethyl-1,2,3,4,5,6,7,8,9,10-decahydro-1,8-acridinedione, whose fluorescence is much higher than that of DDL.

By studying the mechanism for the formation of 3,5-diacetyl-2,6-dihydrolutidine, it has been discovered that a reaction intermediate, 4-amino-3-penten-2-one or Fluoral-P, was capable of reacting rapidly and quantitatively with formaldehyde [Compton B. J., Purdy W. C., Can. J. Chem., 58 (1980) 2207-2211]. However, the specificity of Fluoral-P for formaldehyde, in solution, seems dubious since aldehydes of modest size (up to around 10 carbons) are also capable of reacting rapidly with Fluoral-P [Compton, B. R., Purdy, W. C., Anal. Chem. Acta., 119 (1980) 349-357].

Detection methods based on mixed solid/liquid trapping systems and using Fluoral-P have been developed. One of these systems uses methods of injection of Fluoral-P and formaldehyde in a liquid stream followed by retention of the product formed on a grafted silica support of C18 type impregnated with the elution solvent. According to this method, the analysis is carried out by absorbance or by fluorescence [Teixera, L. S. G., et al., Talanta, 64 (2004) 711-715]

A good sensitivity may be obtained by these detection methods. However, they have a drawback of not allowing the direct detection of the aldehydes in gas form.

Recently, it has been shown that 4-amino-4-phenylbut-3-en-2-one could be used in solution as a specific reactant for formaldehyde in order to form a lutidine derivative [Suzuki Y., Nakano N., Suzuki K., Environ. Sci. Technol., (2003), 37, 5695-5700]. The authors used a device comprising a cellulose filter paper covered with silica granules and impregnated with 4-amino-4-phenylbut-3-en-2-one. Colorimetric detection of the lutidine derivative was carried out by reflectance as the filter paper is not transparent. The sensitivity obtained was 5 ppb with a response time of 15 minutes. This method has the disadvantage of being relatively sensitive to the degree of ambient humidity and to temperature. Specifically, the measurements are impaired when the degree of humidity is outside of a range of 30-700, and/or when the temperature exceeds 35° C. Furthermore, after keeping for more than six months, a reduction in the sensitivity of the impregnated paper is observed. The presence of silica granules which have the particularity of attracting and maintaining the humidity by capillary action makes it possible to explain, at least partly, the fact that the degree of ambient humidity influences this method.

WO 2004/10457.3 describes a sensor capable of detecting formaldehyde in an atmosphere, consisting of a generally polysaccharide gel based, for example, on xanthan gum or gum Arabic, pectin, starch, agar or alginic acid, the gel comprising a Schiff base such as pararosaniline, sulfuric acid or one of its salts, another acid to adjust to pH 3 and water.

U.S. Pat. No. 6,235,532 describes a method of detecting 2-furaldehyde in oil using aniline acetate. The detection is carried out using a porous sol-gel, especially methyltrimethoxysilane, matrix containing aniline acetate.

One of the main problems of the methods of the prior art is that they do not allow the direct and in situ detection and/or quantification of formaldehyde or of other aldehydes in gas form irrespective of the conditions of the environment. Certain methods of the prior art require the withdrawal of samples and the trapping of the gas in liquid/solid phase to enable a qualitative and/or quantitative analysis. Other methods of the prior art are highly sensitive to the degree of ambient humidity or to temperature.

SUMMARY OF THE DISCLOSURE

One subject of the present invention is therefore a method for detecting and/or assaying and/or trapping at least one aldehyde, preferably formaldehyde, which comprises a step of bringing a gas stream into contact with a material comprising a nanoporous metal oxide sol-gel matrix, said matrix containing at least one probe molecule bearing at least one reactive functional group which can react with an aldehyde functional group.

Advantageously, the aldehyde is chosen from formaldehyde, acetaldehyde, propionaldehyde, butryaldehyde, acrolein, pentanal, hexanal and benzaldehyde.

The expression "gas stream" is understood to mean both a gaseous atmosphere or a mixture of gases.

The term "nanoporous" is understood to mean a porous system with pore diameters of less than 100 nm.

The expression "method of trapping" is understood to mean a pollution-control or decontamination method which makes it possible to capture the aldehyde and thus to purify a contaminated environment.

The expression "probe molecule" denotes any organic molecule bearing a reactive functional group whose reaction with an aldehyde functional group leads to a modification of at least one of its physicochemical properties detectable by a suitable analysis technique, preferably a modification of its spectral properties detectable by spectrophotometry.

Preferably, the probe molecule before and/or after reaction with an aldehyde is characterized by spectral properties, especially absorption and/or fluorescence spectra, the variation of which is detectable by a suitable spectrophotometric method known to a person skilled in the art. For example, the probe molecule may be a chromophore whose absorption and/or fluorescence spectra are modified by reaction with an aldehyde. The expression "variation of the absorption and/or fluorescence spectrum" is understood to mean a shift in the wavelength of the absorption and/or fluorescence maxima, or optionally a loss or gain in the absorption or fluorescence intensity at a given wavelength.

According to one preferred embodiment of the invention, the method additionally comprises a step of analyzing the variation of the spectral properties of at least one probe molecule of the material, for example by at least one spectrophotometry technique. The method according to the invention therefore takes advantage of the spectral properties of the probe molecules that have reacted with at least one aldehyde. For this, it is desirable to expose the material to the environment to be tested, said material being advantageously deposited on a suitable substrate. The absorbance and/or fluorescence spectra of the probe molecule before and after possible reaction with the aldehyde will advantageously be compared to determine the presence or absence and/or the amount of aldehyde present in the environment tested.

Furthermore, the method also makes it possible to analyze the overall spectral variations in the material during the reaction of the probe molecule with at least one aldehyde. Advantageously, a person skilled in the art will choose to determine the variation of the fluorescence or that of the absorbance as a function of the aldehyde to be detected and/or quantified.

According to one particular embodiment, it is possible to use surface plasmons in order to enhance the variations in the optical properties of the probe molecules. Specifically, probe molecules, excited by light irradiation, in proximity to a thin layer of metal may be coupled to the surface plasmons and lead to lower detection limits and make it possible to thus detect or assay smaller amounts of aldehyde.

According to another embodiment, the material before and/or after reaction with an aldehyde is characterized by its interaction with Love type waves. The structural modifications linked to the reaction of the probe molecules with the aldehydes result, in particular, in a variation in mass, viscoelasticity, or else dielectric constant which has an impact on the Love waves. This embodiment is generally implemented in the presence of a piezoelectric material or a material on which it is possible to detect and generate Love waves, typically using electrodes made of interdigitated combs in a delay line or resonator configuration.

According to one preferred embodiment, the probe molecule bearing a functional group reactive with an aldehyde functional group is chosen from enaminones and the corresponding β-diketone/amine pairs thereof, imines and hydrazines, or salts derived from these compounds.

According to one embodiment, the probe molecule incorporated into the material of the method according to the invention is an enaminone. The term "enaminone" is understood to mean any molecule which corresponds to the formula (I):

in which:
$R_1$ corresponds to a hydrogen, an alkyl or aryl radical;
$R_2$ corresponds to a hydrogen;
$R_3$ corresponds to a hydrogen, an alkyl or aryl radical;
$R_4$ corresponds to a hydrogen, an alkyl or aryl radical; and
$R_5$ corresponds to a hydrogen.

An alkyl radical may optionally be monosubstituted or polysubstituted, linear, branched or cyclic, saturated or unsaturated, a $C_1$-$C_{20}$, preferably $C_1$-$C_{10}$ alkyl radical, the substituent or substituents possibly containing one or more heteroatoms such as N, O, F, Cl, P, Si or S. Among such alkyl radicals, mention may especially be made of methyl, ethyl, propyl, isopropyl, butyl, isobutyl, tert-butyl and pentyl radicals. Mention may also be made, among the unsaturated alkyl radicals, of ethenyl, propenyl, isopropenyl, butenyl, isobutenyl, tert-butenyl, pentenyl and acetylenyl radicals.

An aryl radical may be an aromatic or heteroaromatic, monosubstituted or polysubstituted carbon-based structure composed of one or more aromatic or heteroaromatic rings each comprising from 3 to 8 atoms, the heteroatom possibly being N, O, P or S.

Optionally, when the alkyl or aryl radicals are polysubstituted, the substituents may be different from one another. Among the substituents of the alkyl and aryl radicals, mention may especially be made of halogen atoms, alkyl, haloalkyl, substituted or unsubstituted aryl, substituted or unsubstituted heteroaryl, amino, cyano, azido, hydroxy, mercapto, keto, carboxy, etheroxy and alkoxy, such as methoxy, groups.

Advantageously, $R_1$ and $R_3$ are independently a methyl, ethyl, isopropyl, butyl, isobutyl, tert-butyl, pentyl or phenyl radical and $R_4$ a hydrogen Advantageously, $R_1$ is a methyl radical, $R_2$ a hydrogen, $R_3$ a methyl or phenyl radical and $R_4$ a hydrogen.

According to one particularly preferred embodiment, the enaminone chosen as a probe molecule is 4-amino-3-penten-2-one (Fluoral-P) due to its high specificity for formaldehyde Fluoral-P has an absorption spectrum ($\mu_{max}$=302 nm) different from that of the reaction product, DDL ($\lambda_{max\ 1}$=206 nm and $\lambda_{max\ 2}$=415 nm) In this case, the detection may advantageously be carried out by measuring the variation of the absorbance at a wavelength of 415 nm, at which only the DDL absorbs. Furthermore, as DDL has fluorescence properties, its detection and its assaying may be carried out by exciting it, especially at 415 nm, and by measuring the fluorescence intensity at a given wavelength ($\lambda_{max}$ of fluorescence at 502 nm) or the total fluorescence (integrated over the entire spectrum) as a function of time.

The β-diketone/amine pair corresponding to the enaminone described previously may also be considered as a probe molecule in its own right. The enol form of the β-diketone is considered as an equivalent form; it is customary, in effect, to find a thermodynamic equilibrium between these two forms. Since the reaction mechanisms are not exactly elucidated, it appears that a β-diketone/amine pair corresponding to the enaminone described previously will react with an aldehyde, and preferably with formaldehyde. The expression "β-diketone/amine pair" is understood to mean any pair of molecules which corresponds to the formula (II):

in which $R_1$, $R_2$, $R_3$, $R_4$ and $R_5$ have the meaning already given above,
the amine possibly being replaced by its corresponding ammonium salt.

The amine may be quaternized and then the counterion may be chosen from the counterions known to a person skilled in the art and that are most suitable for the reactants. Among the preferred ammonium salts, mention may especially be made of acetates, sulfates, halides, and particularly chlorides and tetrafluoroborates.

According to another preferred embodiment, at least one imine is incorporated, as a probe molecule, into the material of the method according to the invention. The chosen imine may be, for example, fuchsin or pararosaniline, advantageously the imine will be chosen from Schiff bases and more particularly from acridine yellow, methyl yellow or dimethyl yellow.

According to another preferred embodiment, at least one hydrazine is incorporated into the material of the method according to the invention. The term "hydrazine" is understood to mean any molecule which corresponds to the formula (III):

in which:
$R_6$ corresponds to a hydrogen, a $C_1$-$C_{20}$, preferably $C_1$-$C_{10}$, alkyl radical, more preferably a methyl, ethyl, isopropyl, butyl, isobutyl, text-butyl and pentyl radical, a $C_3$-$C_{16}$ aryl radical, especially a phenyl and arylsulfonyl radical; and
$R_7$ corresponds to a $C_3$-$C_{16}$ aryl radical, especially a phenyl and arylsulfonyl radical.

Advantageously, the hydrazine of the material according to the invention is chosen from 2,4-dinitrophenylhydrazine (DNPH), 2-hydrazinobenzothiazole, 3-methyl-2-benzothiazolinone, 5-(dimethylamino)naphthalene-1-sulfonylhydrazine, 1-methyl-1-(2,4-dinitrophenyl)hydrazine, N-methyl-4-hydrazino-7-nitrobenzofurazan and hydralazine.

The probe molecule bearing a reactive functional group which can react with at least one aldehyde is incorporated within a nanoporous metal oxide sol-gel matrix. The expression "nanoporous metal oxide sol-gel matrix" is understood to mean a nanoporous polymeric network produced from at least one metal oxide of formula (IV):

$$M(X)_m(OR_8)_n(R_9)_p$$

in which:

M corresponds to a metal chosen from silicon, aluminum, titanium, zirconium, niobium, vanadium, yttrium and cerium;

$R_8$ and $R_9$ correspond independently to an alkyl or aryl radical such as defined above;

n, m and p are integers, such that their sum is equal to the valency of M and that n is greater than or equal to 2; and X is a halogen, preferably chlorine.

According to one preferred embodiment, the metal M of the oxide that is a precursor of the sol-gel matrix is silicon or zirconium.

According to one particularly preferred embodiment, the metal oxide is $Si(OMe)_4$.

Furthermore, the inventors have demonstrated that the choice of the metal oxide forming the porous matrix conditions the size of the pores and the accessibility of the aldehydes to the probe molecules. Thus, it is preferable to use matrices produced from metal oxides of general formula (III) for which $R_8$ and $R_9$ are alkyls and preferably methyl or ethyl radicals in order to specifically detect and/or assay formaldehyde. On the other hand, for a method of trapping an aldehyde in a contaminated environment, the size of the pores will advantageously be larger in order to facilitate the dispersion of the gaseous medium within the matrix.

According to one particular embodiment, in order to make the nanoporous network more hydrophobic, it is preferable that p be at least equal to 1.

For the implementation of the above method, the inventors have developed novel materials capable of reacting with at least one aldehyde. This is why another subject of the present invention is a material capable of reacting with at least one gaseous aldehyde comprising a nanoporous sol-gel matrix containing at least one probe molecule bearing a functional group reactive with an aldehyde functional group.

Under preferred conditions of the invention, the material is characterized as indicated above.

Preferably, the radicals $R_8$ and $R_9$ of the metal oxide that is a precursor of the nanoporous sol-gel matrix are independently methyl or ethyl radicals and the probe molecule is an enaminone.

More preferably, the material according to the invention comprises, as a metal oxide, a polymer of $SiO_2$ advantageously prepared from $Si(OMe)_4$, and Fluoral-P as a probe molecule. Such a material is particularly advantageous for the specific detection and/or assaying of gaseous formaldehyde.

The invention also relates to a process for preparing the above material comprising:

(a) a step of producing a nanoporous sol-gel matrix by polymerization of at least one metal oxide such as defined above; and (b) a step of incorporating into said nanoporous sol-gel matrix or into said at least one metal oxide, at least one probe molecule such as defined above.

The sol-gel matrix of the material according to the invention may be produced according to a sol-gel process. Grouped under the generic name "sol-gel process" are techniques which make it possible, by simple polymerization of molecular precursors, especially including metal oxides, to obtain polymeric matrices at temperatures close to ambient temperature (20 to 35° C.) The chemical reactions, i.e. hydrolysis and condensation, that are the basis of sol-gel processes, are started when the molecular precursors are brought into the presence of water: the hydrolysis of the oxides takes place first, then the condensation of the hydrolyzed products leads to gelling of the matrix.

According to one preferred embodiment of the method according to the invention, the step of producing the porous sol-gel matrix (a) comprises a step of hydrolyzing at least one metal oxide, said hydrolysis step preferably being carried out in the presence of an organic solvent, such as an alcohol, for instance methanol or ethanol. Advantageously, the hydrolysis step is carried out at a pH below 7 using an inorganic acid such as HCl or $H_2SO_4$.

During the condensation, the hydrolyzed products react together to form polymers which do not stop growing until a three-dimensional polymeric network is obtained. At first, the metal oxide clusters remain in suspension without precipitating; this is the sol. These clusters gradually occupy an increasing large volume fraction. The viscosity then becomes high and the liquid finishes by gelling into a matrix. The matrix thus obtained is therefore composed of a polymeric network which has a porosity that can be varied.

Advantageously, the diameter of the pores of the sol-gel matrix may also be adjusted by choosing particular metal oxides. The inventors especially consider that metal oxides of formula (IV) for which $R_8$ and $R_9$ are alkyls, preferably methyl or ethyl radicals, make it possible to create matrices whose pores have a reduced diameter. When it is desired to detect a small-size aldehyde, especially formaldehyde, it then becomes particularly advantageous to produce a matrix having pores of a reduced diameter which will specifically trap the small-size aldehyde, and more particularly formaldehyde.

Advantageously, the step of producing the sol-gel matrix (a) and that of incorporating at least one probe molecule (b) will be carried out simultaneously. This is because the preparation conditions are gentle enough for the probe molecules to be incorporated into the sol-gel matrix without being altered.

According to one preferred embodiment, the method according to the invention additionally comprises a homogenization and/or drying step. The drying step enables, amongst other things, the evaporation of the water and of the alcohols of the matrix. Advantageously, provision is made for the incorporation of at least one probe molecule before the homogenization step, more preferably during the hydrolysis step.

According to another preferred embodiment, the incorporation of at least one probe molecule could be carried out in the nanoporous matrix either by impregnation in solution or in the vapor phase according to techniques that are well known to a person skilled in the art, especially including sublimation.

For the implementation of the method of detecting and/or assaying and/or trapping at least one aldehyde, the material according to the invention may be integrated in devices or sensors. The present invention therefore also relates to any device or sensor specific to gaseous aldehydes, preferably formaldehyde, characterized in that it comprises at least one material conforming to the invention or obtained according to the preparation method conforming to the invention.

According to one preferred embodiment, a sensor comprises at least one material conforming to the invention deposited on a suitable substrate, preferably in the form of a thin film on a transparent substrate. The substrate may be chosen from those commonly used in the field of spectrophotometric analysis, especially including slides or plates made of glass, quartz, mica or fluorspar. Typically, the deposition is carried out according to techniques well known to a person skilled in the art including, in particular, dip coating, spin coating or (liquid or gas) spraying. Advantageously, the deposition of the material according to the invention is carried out by dip coating. A person skilled in the art will adjust the rate of removal of the substrate from the deposition of the material which is deposited, preferably a rate close to 25 mm/min. The dip coating may be carried out at ambient temperature (22-25° C.) with a relative humidity of the air between 15 and 50%.

Figure 11:
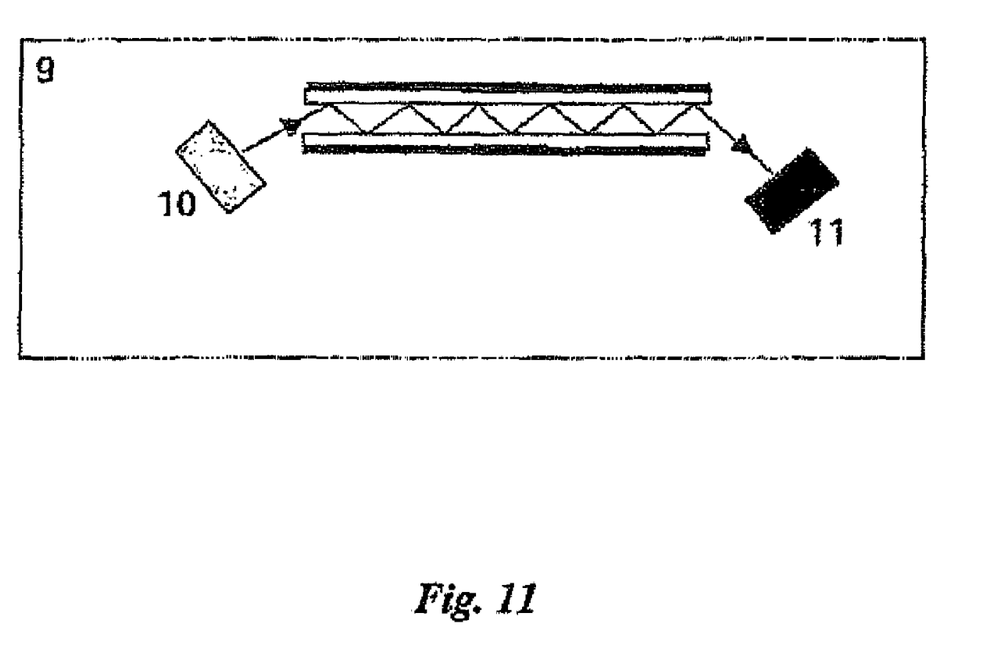
FIG. 11 represents a detection system integrated into a sensor comprising two films composed of the material.

According to another preferred embodiment, the devices or sensors (FIGS. 8 to 11) according to the invention integrate at least one source of light excitation (10) and a collector (11). They are composed of a first compartment (4) and a second compartment (5) and a screen (7). The gas is introduced into the sensor via a specific inlet (1) then passes through a thermostat which makes it possible to control the temperature, and also a particulate filter (3). A delivery pump system (8) makes it possible to accelerate the diffusion of the gas to the material according to the invention (9). Alternatively, the pump may be placed near the gas outlet (2) rather than close to the inlet, in this case a micropump will advantageously be used. It should be specified that the material according to the invention (9) is protected from the outside by a protective envelope (13) in a leaktight manner by an o-ring (12). When it is a question of an aldehyde, this will react on the probe molecule. The reaction of the aldehyde with the probe molecule will be detected after light excitation (10) by a collector (11) and read on the screen (7). Advantageously, the light source will be composed of a halogen lamp or a light-emitting diode and the collector of a diode strip or a low-voltage photomultiplier. When the detection method is based on a variation in absorbance of the doped film, it is preferable to use a system composed of two thin doped films each deposited on a reflective substrate in order to optimize the absorption of the light source by the material. The photons, by rebonding multiple times off the film-covered walls, will be strongly absorbed by the material (FIG. 11). A gas outlet (2) is provided in the frame of this sensor. Miniaturized devices or sensors are preferred. It is desirable that the device or sensor comprises, in addition, a support for the materials according to the invention, more particularly a support that accommodates the chosen substrate as a function of the detection method. Advantageously, the device or sensor will also comprise a system for accelerating the diffusion of the medium to be analyzed, particularly a gaseous medium. Preferably, the system for accelerating the diffusion of the gas is a pneumatic system such as a piston, a delivery pump or a micropump. Such a system will be particularly useful in the case of a pollution-control device. The invention thus particularly relates to aldehyde sensors with direct optical transduction.

According to one particular embodiment, it is possible to use a specific substrate which makes it possible to generate surface plasmons. A device that makes it possible to benefit from the surface plasmons will contain, for example, a sheet chosen from the substrates commonly used in the field of spectrophotometric analysis, especially including slides or plates made of glass, quartz, mica or fluorspar, said plate being covered with a layer of metal on which the material according to the invention is deposited.

Among the metals that can be used, mention may be made of gold, silver or preferably aluminum. The choice of metal is generally linked to that of the probe molecule; thus, for example, for UV-absorbing probe molecules it is preferable to use aluminum which has a UV emission linked to the plasmons [J. Phys. Chem. B, 2004, 108, 19114-19118]. The thickness of the metal layer may be between 10 and 90 nm, preferably around 60 nm. It is advantageous to deposit a layer of material that is free from the probe molecule between the layer of metal and the layer of material in order to prevent a probe molecule from being in direct contact with the metallized surface. Typically, the layer of material will have a thickness between 5 and 40 nm, preferably around 25 nm, and the layer of material that is free from the probe molecule will have a thickness between and 20 nm, preferably 10 nm. The irradiation wavelength will depend on the nature of the metal and on the fluorescent probe molecule. Typically, UV sources (260-300 nm for Al films and 350-400 nm for Ag films) will be used to generate the plasmons.

According to another particular embodiment, the variations in the mass, viscoelasticity or dielectric constant of the material are studied using Love type waves, especially by the variation in their phase velocity or their propagation velocity.

It is recommended to use a piezoelectric substrate, deposited on which will be electrodes with interdigitated comb structures (or transducers). These electrodes may be positioned at the two ends of the substrate surface and the nanoporous material is positioned in the free space between the two electrodes, according to a "delay line" configuration. Love type waves may then be generated by the transducers and the variation in their propagation velocity may, for example, be monitored by the transducers.

Typically, the piezoelectric substrate equipped with transducers could be covered by a guide coat, for example made of $SiO_2$, and the nanoporous material deposited on the surface of this guide coat.

The material according to the invention has numerous advantages which enable it to be used in the metrology of gaseous aldehydes, and more particularly of gaseous formaldehyde, and also in pollution control. Due to its preparation method, the material according to the invention is nanoporous and therefore offers a very large specific surface area for adsorption. This structural characteristic is even more important in the context of the pollution-control device. Furthermore, the size of the pores and the nature of the material according to the invention may easily be adjusted for selectively detecting and/or assaying certain aldehydes, especially including formaldehyde. The material according to the invention may be used in the methods for detecting and/or assaying and/or trapping gaseous aldehydes irrespective of the conditions, especially including the degree of ambient humidity. The invention does not require the presence of acid nor working at a particular pH. For example, the invention may be implemented between pH 4 and 10, especially between pH 4 and 7.

Lastly, the material according to the invention may easily be integrated into a sensor or a device which allows in situ, direct and simple detection of gaseous aldehydes Advantageously, sensors may be used in a network and to permanently ensure the quality control of an environment at high risk of contamination by aldehydes. The devices or sensors may also be combined with a visual or audible alarm which is activated when the aldehyde content in the environment to be tested reaches a certain critical threshold.

BRIEF DESCRIPTION OF THE DRAWINGS

The invention will be understood more accurately through the appended figures and exemplary embodiments which follow.

DETAILED DESCRIPTION

Examples

The spectrophotometric measurements were carried out on a UNICAM 500 spectrophotometer and a SPEX-FLUO-ROLOG 3 spectrofluorometer.

Example 1

Preparation of a Material Comprising a Nanoporous Sol-Gel Matrix

Fluoral-P could be synthesized according to the method developed by Lacey. [Lacey, Aust. J. Chem., 23 (1970) 841-842]. For the set of formaldehyde exposure experiments, the velocity of the gas stream was kept equal to 200 ml/min unless specified otherwise.

The incorporation of Fluoral-P into the porous matrices based on a metal oxide was carried out according to the "one-pot" method of the sol-gel process. A matrix according to the invention was produced from tetramethoxysilane (TMOS) in an ethanol/water solution. The TMOS/ethanol/water molar proportions were equal to 1/4/4. A 0.5 mol/l ethanolic solution of Fluoral-P, added to which were TMOS and an aqueous solution of acid (HCl such that pH=1). After addition of the Fluoral-P, the solution obtained was homogenized by ultrasonic means for 10 minutes.

Example 2

Deposition of the Material on a Suitable Support

A thin homogeneous film of the material prepared in Example 1 was then deposited on a quartz substrate (0.8×0.1× 15 mm) by the dip-coating method with a film removal rate of around 25 mm/min. The deposition was carried out at ambient temperature (22-25° C.) with a relative humidity of 15 to 50%.

The deposit (30 nm) could also be obtained in a similar manner on a quartz substrate previously coated with a layer of silver or aluminum (60 nm) and a layer of matrix according to the invention was produced from tetramethoxysilane (TMOS) (10 nm) in order to carry out a study using plasmons.

It is possible to carry out a deposition of the nanoporous material on a piezoelectric substrate, deposited on which, at the two ends, are electrodes in an interdigitated comb structure acting as transducers, and previously coated with an $SiO_2$ guide coat, in order to carry out a study using Love waves.

Example 3

Use of the Material for Selective Detection of Formaldehyde

The sample was then placed in a flow cuvette (10×10×40 mm) having four optical faces equipped with a 4 mm diameter tubular outlet and inlet. The gas mixtures were generated from a permeation oven containing a permeation tube filled with paraformaldehyde (solid trimer of formaldehyde) which was heated at 90° C. to release the formaldehyde vapors which were carried by nitrogen. The initial content of formaldehyde in a 125 ml/min stream was 4 ppm. The concentration and the flow of the final mixture were controlled and adjusted by a dilution system. Similar, the relative humidity of the mixture could be varied by injection of water vapor adjusted using a flowmeter.

Figure 1:
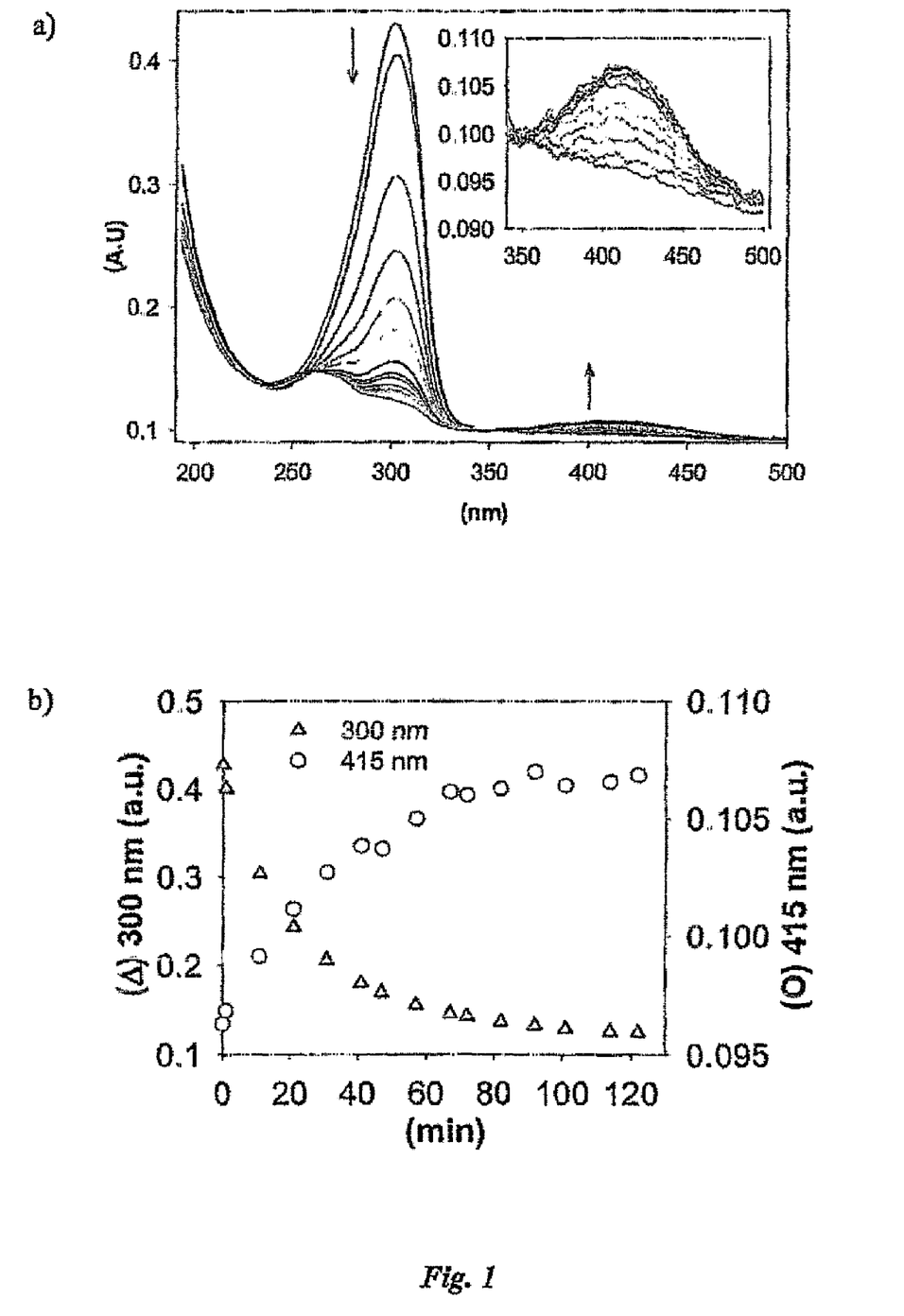
FIG. 1(a) represents an absorbance spectrum (in arbitrary units a.u.) as a function of the wavelength (nm) observed over time during exposure of a porous film containing Fluoral-P to a nitrogen stream containing 8 ppb of formaldehyde with a relative humidity of the gas mixture of 58%.
FIG. 1(b) represents a curve illustrating the variation in absorbance of Fluoral-P (at 300 nm) and of DDL (at 415 nm) as a function of the exposure time (in min).
Figure 2:
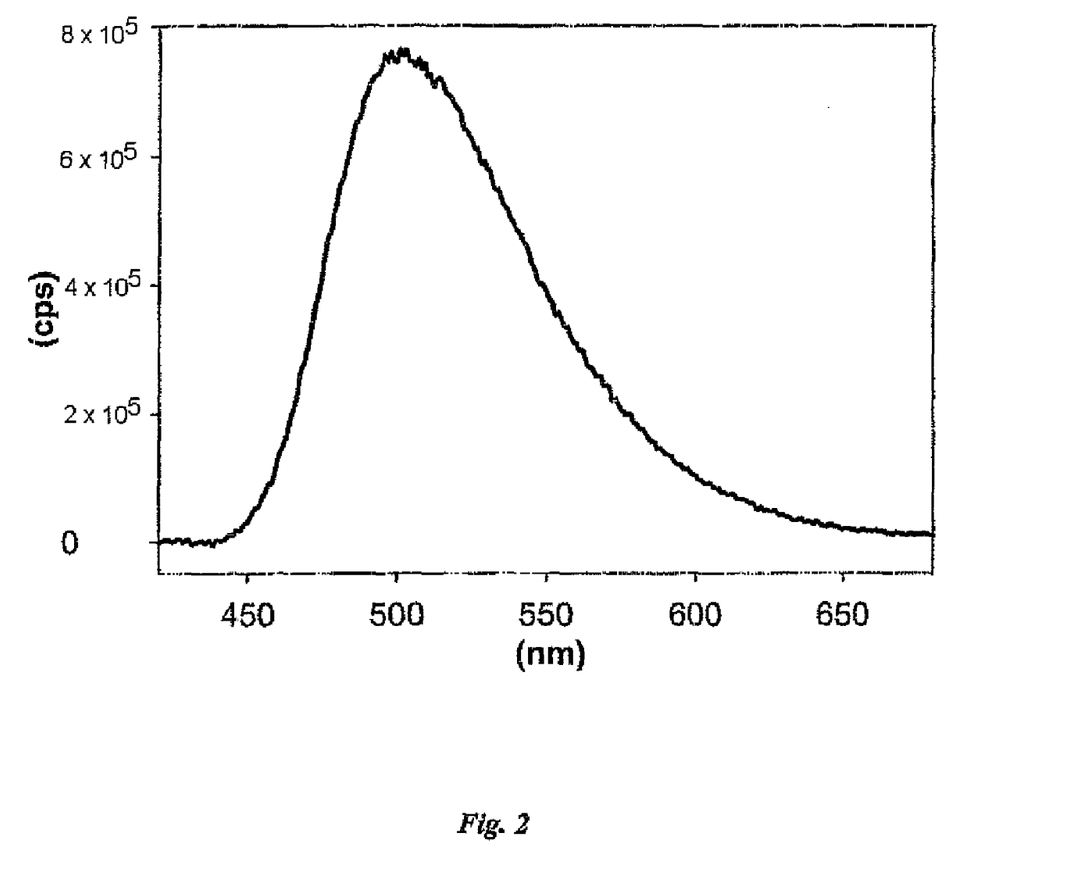
FIG. 2 represents a fluorescence spectrum as a function of the wavelength (nm) of 3,5-diacetyl-2,6-dihydrolutidine (reaction product of Fluoral-P with formaldehyde) measured at the end of the experiment when the absorbance at 415 nm reaches a plateau. The fluorescence intensity is measured as the number of counts per second (cps).

The reaction of two molecules of Fluoral-P with formaldehyde formed DDL. Absorption measurements (FIG. 1) and fluorimetric measurements (FIG. 2) were carried out on the sample thus prepared. Fluoral-P had an absorption spectrum ($\lambda_{max}$=302 nm) different from that of DDL ($\lambda_{max\ 1}$=206 nm and $\lambda_{max\ 2}$=415 nm), the detection could in this case advantageously be carried out by measuring the variation in absorbance at 415 nm, where only DDL absorbed. Furthermore, since DDL had fluorescence properties, its detection and therefore the assaying of formaldehyde, could be carried out by illuminating the film, especially at 415 nm, so as to excite the DDL and by collecting the fluorescence intensity at a given wavelength ($\lambda_{max}$ of fluorescence at 502 nm) or the total fluorescence (integrated over the entire spectrum) as a function of time. The fluorescence spectrum from FIG. 2 corresponded to the end of the exposure when all the Fluoral-P had reacted.

Figure 3:
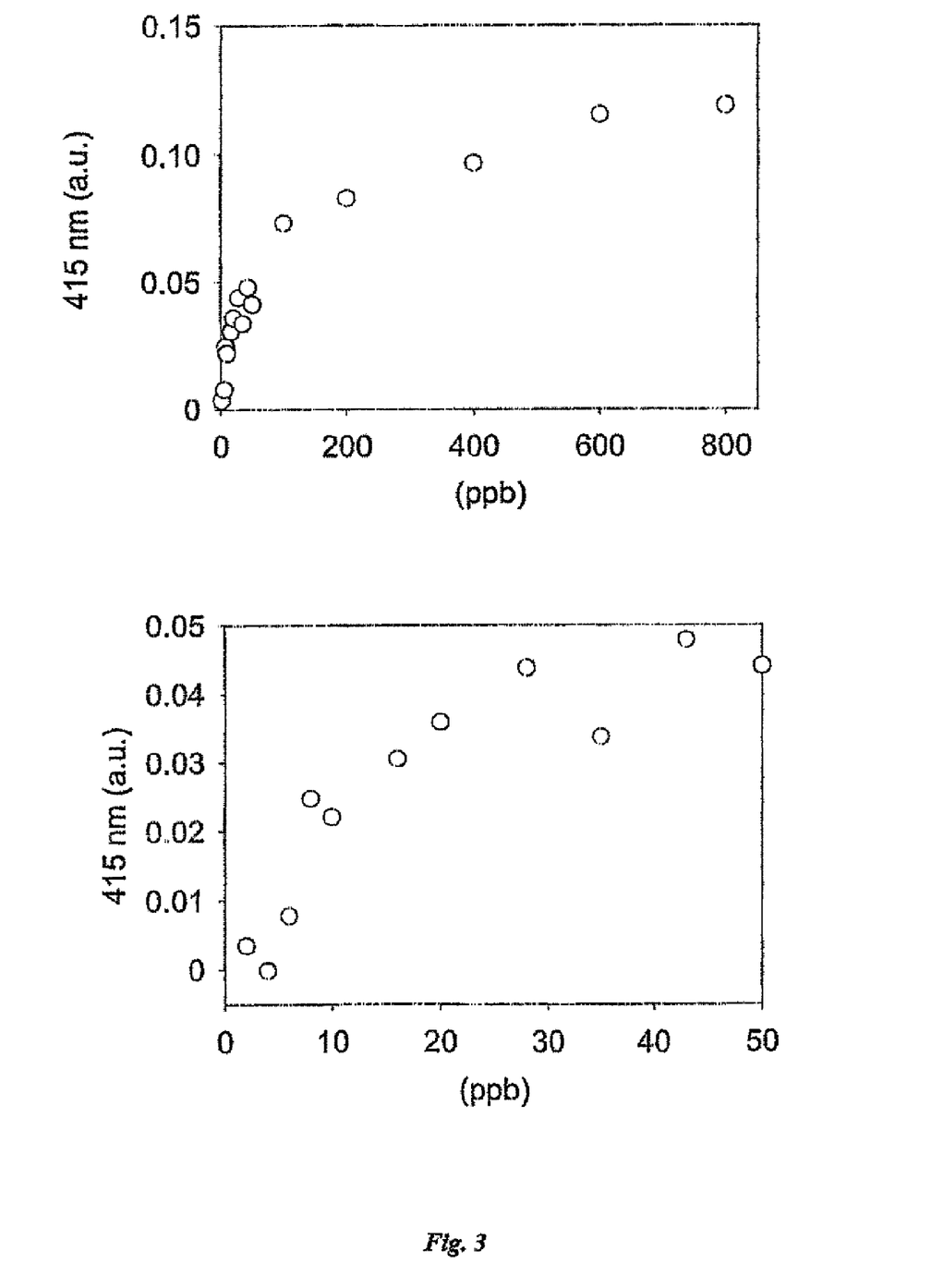
FIG. 3 represents a curve illustrating the variation in the absorbance (a.u.) at 415 nm as a function of the concentration (in parts per billion, ppb) of 3,5-diacetyl-2,6-dihydrolutidine measured after complete consumption of the Fluoral-P, the velocity of the gas stream is 200 ml/min and the relative humidity is 58%.

It appears that the trapping efficiency of formaldehyde in the porous matrix and its reactivity with Fluoral-P vary as a function of its concentration in the gas mixture. From FIG. 3, variations in the absorbance as a function of the formaldehyde concentration in the medium can be seen; each point represents one experiment carried out at a given formaldehyde content.

Figure 4:
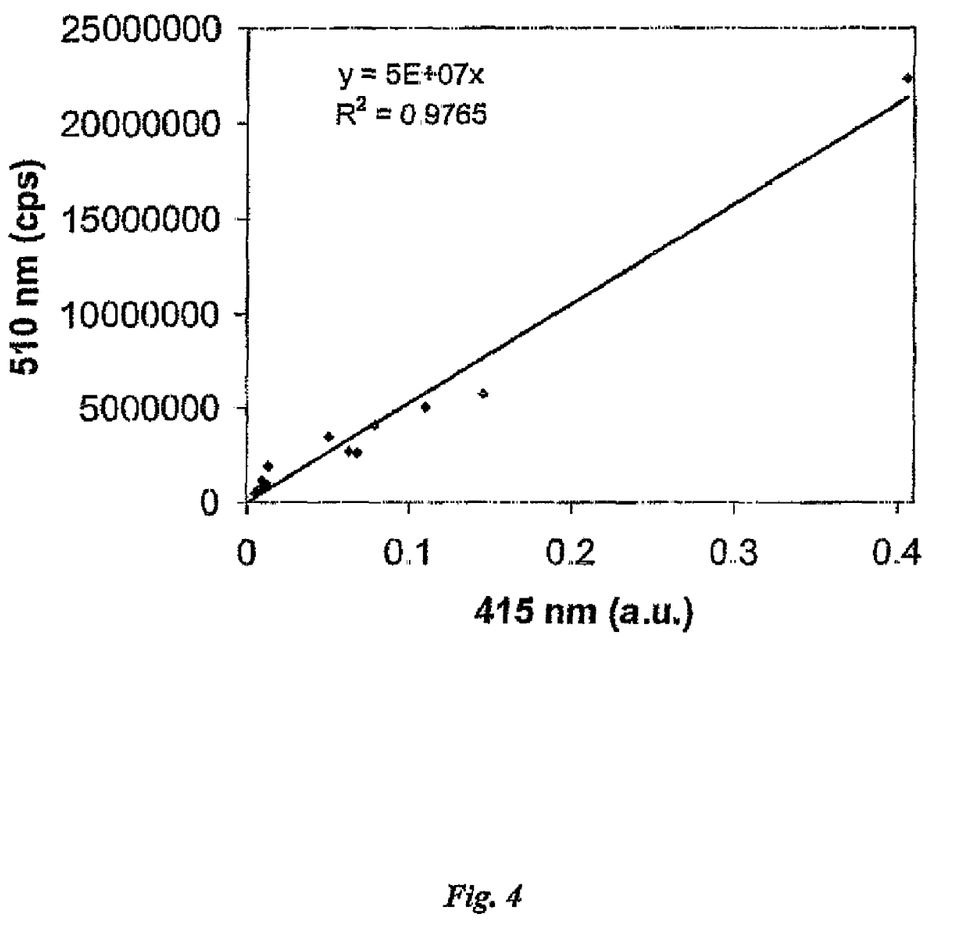
FIG. 4 represents the variation in the fluorescence intensity (cps) of 3,5-diacetyl-2,6-dihydrolutidine at 510 nm as a function of its absorbance (a.u.) at 415 nm; the values were obtained from the exposure, in a stream, of various films containing Fluoral-P for various formaldehyde contents in nitrogen with a relative humidity maintained at 58% and a gas stream of 200 ml/min for all the experiments.

It is verified that the fluorescence intensity of the 3,5-diacetyl-2,6-dihydrolutidine, measured at 510 nm, is proportional to its absorbance at the excitation wavelength, 415 nm, as in solution (FIG. 4), which clearly shows that only DDL absorbs at 415 nm and fluoresces at 510 nm.

It appears that the use of materials according to the invention makes it possible, via fluorimetry, to detect 2 ppb of formaldehyde over 100 minutes. This is the plateau attained. The detection can be seen from the first measurements with a 200 ml/min stream of a nitrogen mixture containing 2 ppb of formaldehyde, namely for a total volume of nitrogen of 20 liters. When the formaldehyde content is 50 ppb, only 5 minutes are required for a total volume of 1 liter.

The response time of the analysis is limited here by the experimental dilution device which does not allow a flow rate of 200 ml/min to be exceeded. An increase of the flow rate to 1 or 2 l/min should reduce this time by a factor of 5 to 10.

Furthermore, the sensitivity can be greatly increased in the fluorimetric measurements, in particular, by exciting the 3,5-diacetyl-2,6-dihydrolutidine in the whole of its absorption band between 360 and 470 nm and by collecting the integrated fluorescence over the entire fluorescence spectrum. The use of optical interference filters for delimiting the excitation wavelength range and the emission collection range would make it possible to avoid using a spectrophotometer and therefore to reduce the cost of the detection equipment.

Similar experiments were carried out using the ambient air of the laboratory as the carrier gas. The pollutants present, and especially the traces of organic solvents such as ethanol (around 500 ppb) or acetone (around 500 ppb) and pollutants such as $NO_2$, did not have any impact on the measurements.

The use of surface plasmons resulted in a spectrum for which it was possible to observe a multiplication of the peaks or an enhancement of the intensity. Thus, the excitation at 295 nm of a 20 nm Al film on which a 10 nm layer of $SiO_2$ was deposited, generated plasmons around 300-450 nm. For a 60 nm Ag film, on which a 20 nm $Al_2O_3$ film was deposited, and which was excited between 350-400 nm, plasmons were generated around 450-650 nm.

It has furthermore been observed that the variation in the propagation velocity of Love waves, generated using the piezoelectric substrate, was a function of the amount of aldehyde which had reacted with the material.

Considering the efficiency of the reaction, such a device appears to be usable for the pollution control of an atmosphere contaminated by formaldehyde.

Example 4

Preparation of a Material Containing 2,4-Dinitrophenylhydrazine

The incorporation of 2,4-dinitrophenylhydrazine (supplier: FLUKA) into porous films based on inorganic polymers was carried out according to the "one-pot" method of the sol-gel process. Two, ethanolic and aqueous acidic (pH=1), stock solutions saturated with 2,4-dinitrophenylhydrazine were first prepared. The sol was composed of the tetramethoxysilane (TMOS)/ethanol stock solution/aqueous acidic stock solution mixture in molar proportions equal to 1/4/4.

Example 5

Deposition of the Material on a Support by a Dip-Coating Method

A thin homogeneous film of the material prepared in Example 4 was then deposited on a quartz substrate (0.8×0.1× 15 mm) by the dip-coating method with a film removal rate of around 25 mm/min. The deposition was carried out at ambient temperature (22-25° C.) with a relative humidity of 15 to 50%.

Example 6

Figure 5:
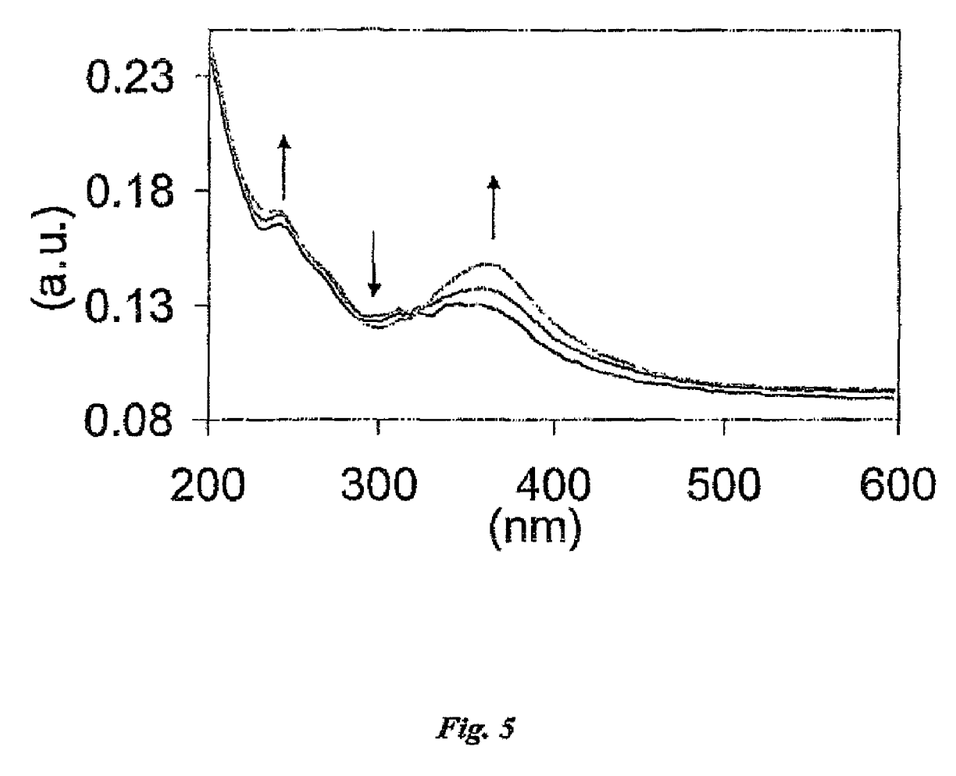
FIG. 5 represents the variation in the absorbance (a.u.) as a function of the wavelength (nm) during the exposure of a thin porous film containing 2,4-dinitrophenylhydrazine to a mixture of nitrogen containing 800 ppb of formaldehyde, the relative humidity is maintained at 58% and the gas stream is 200 ml/min; the various curves correspond to t=0, 1 and 61 min.
Figure 6:
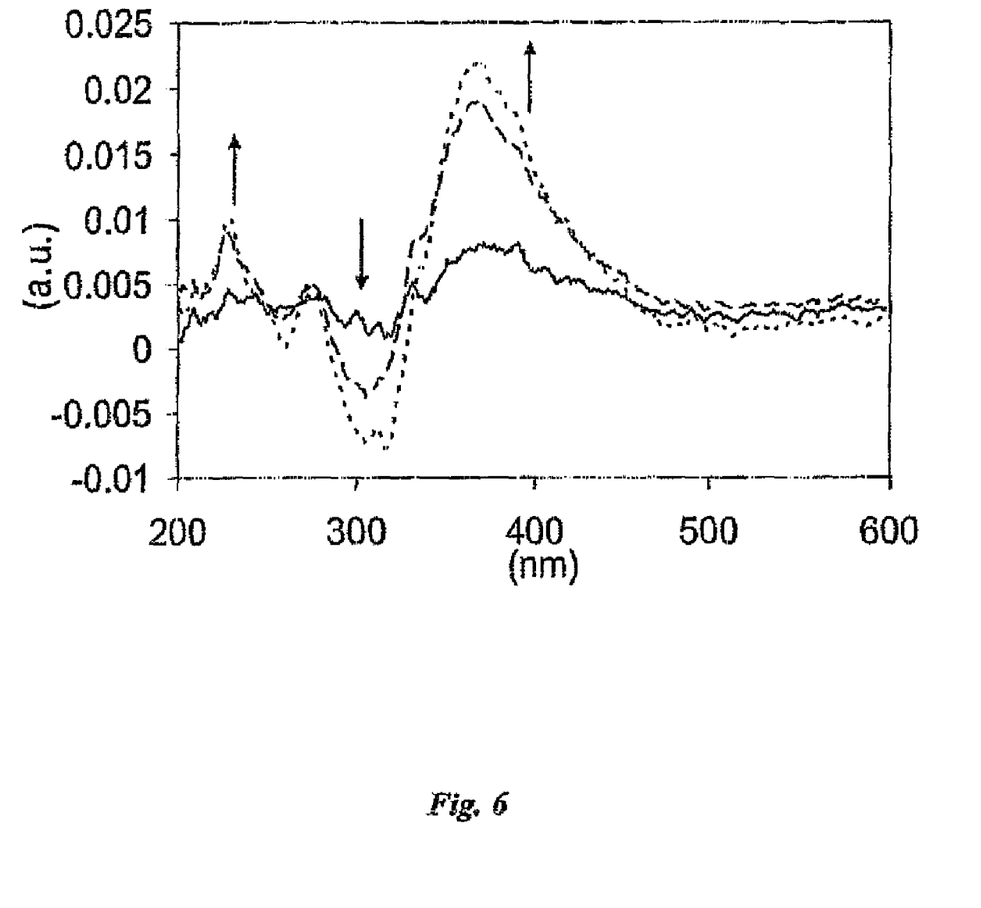
FIG. 6 represents the variation in the differential absorbance (a.u.) as a function of the wavelength (nm) during the exposure of a thin porous film containing 2,4-dinitrophenylhydrazine to a mixture of nitrogen containing 800 ppb of formaldehyde, the relative humidity is maintained at 58% and the gas stream is 200 ml/min.
Figure 7:
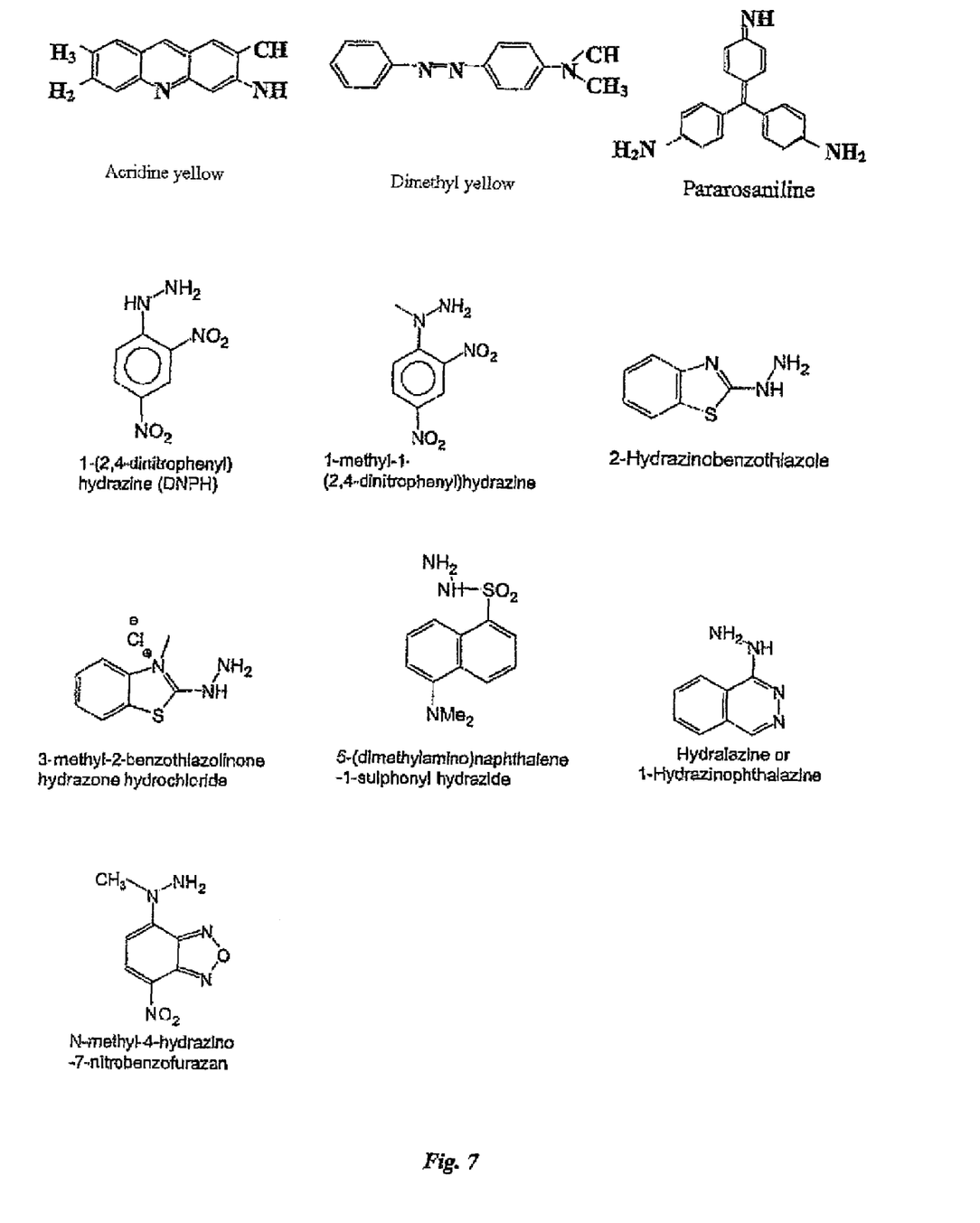
FIG. 7 corresponds to a list of probe molecules which can be used within the context of the invention.
Figure 8:
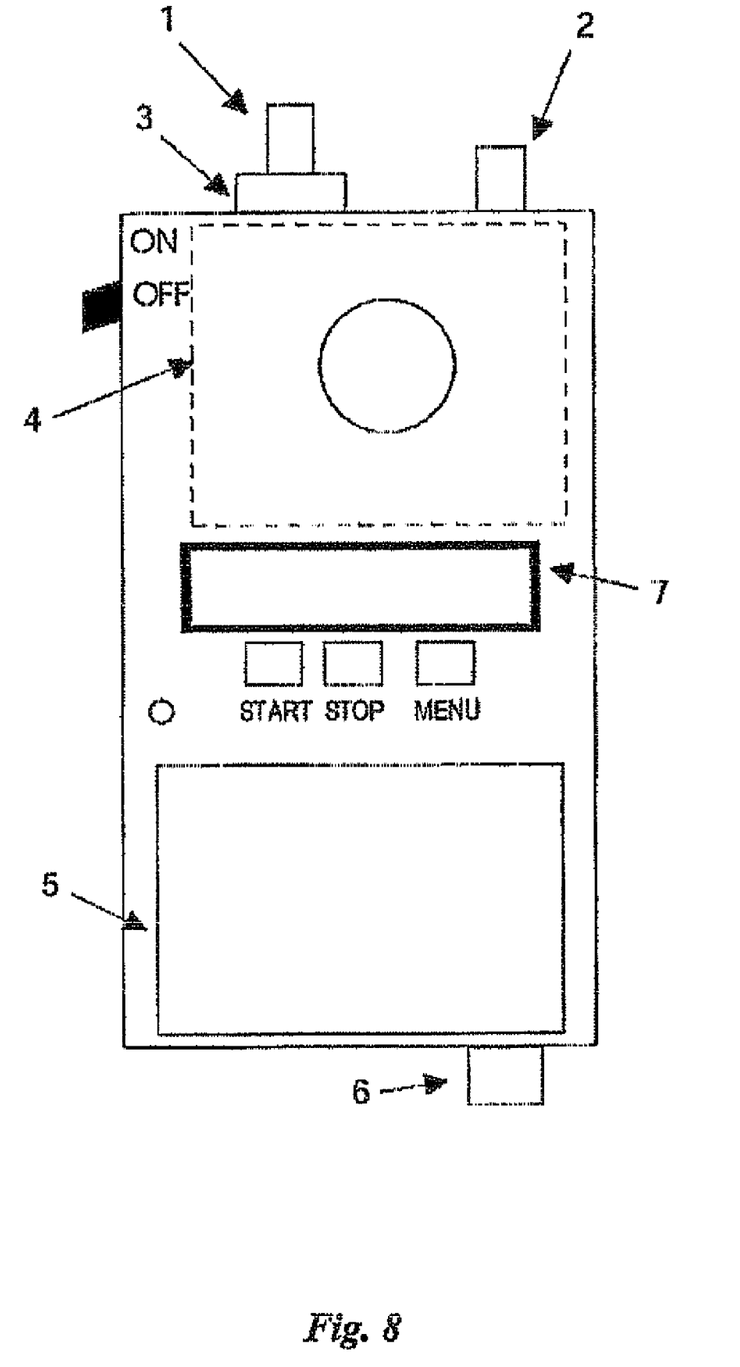
FIG. 8 corresponds to the diagram of a sensor according to the invention.
Figure 9:
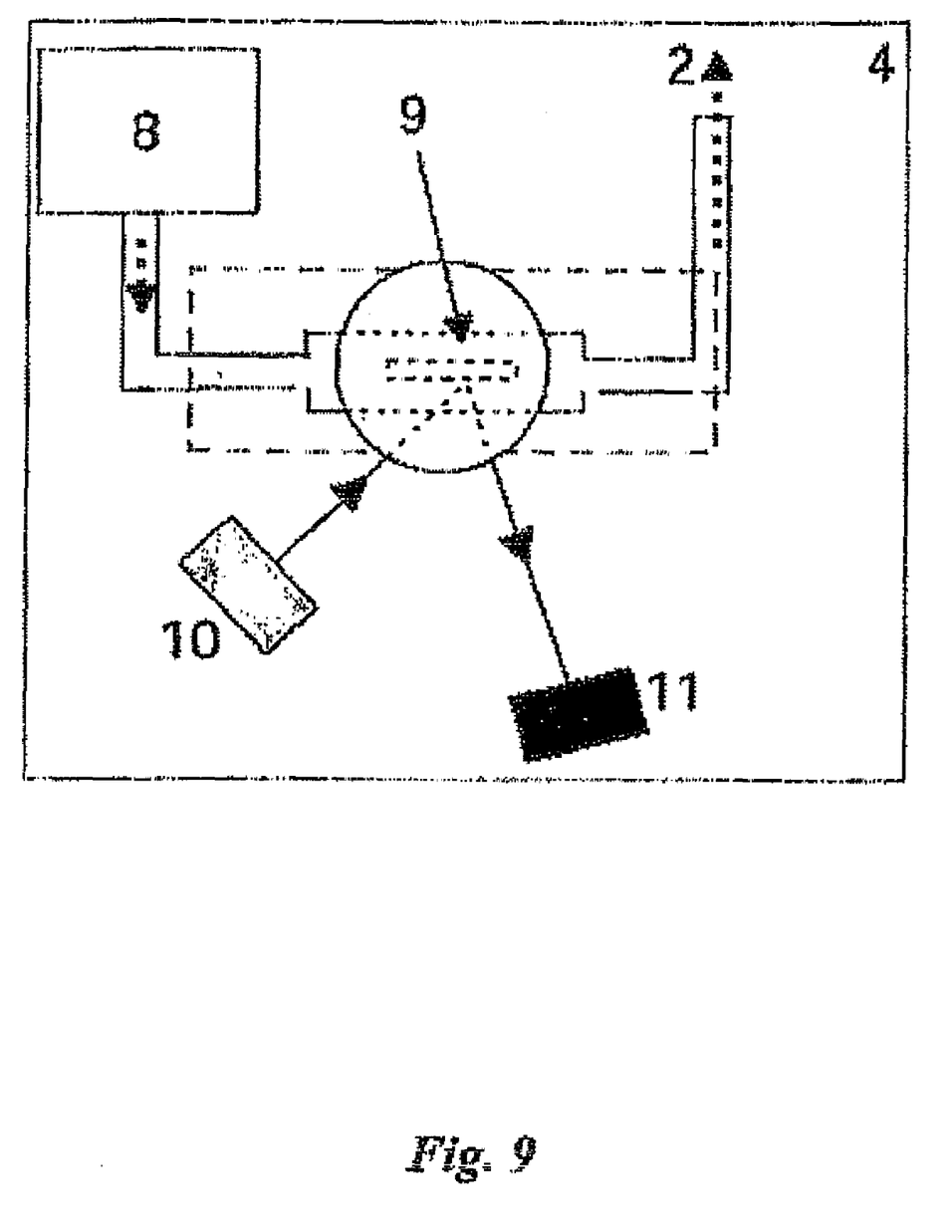
FIG. 9 represents a top view of compartment (4) of a sensor according to the invention.
Figure 10:
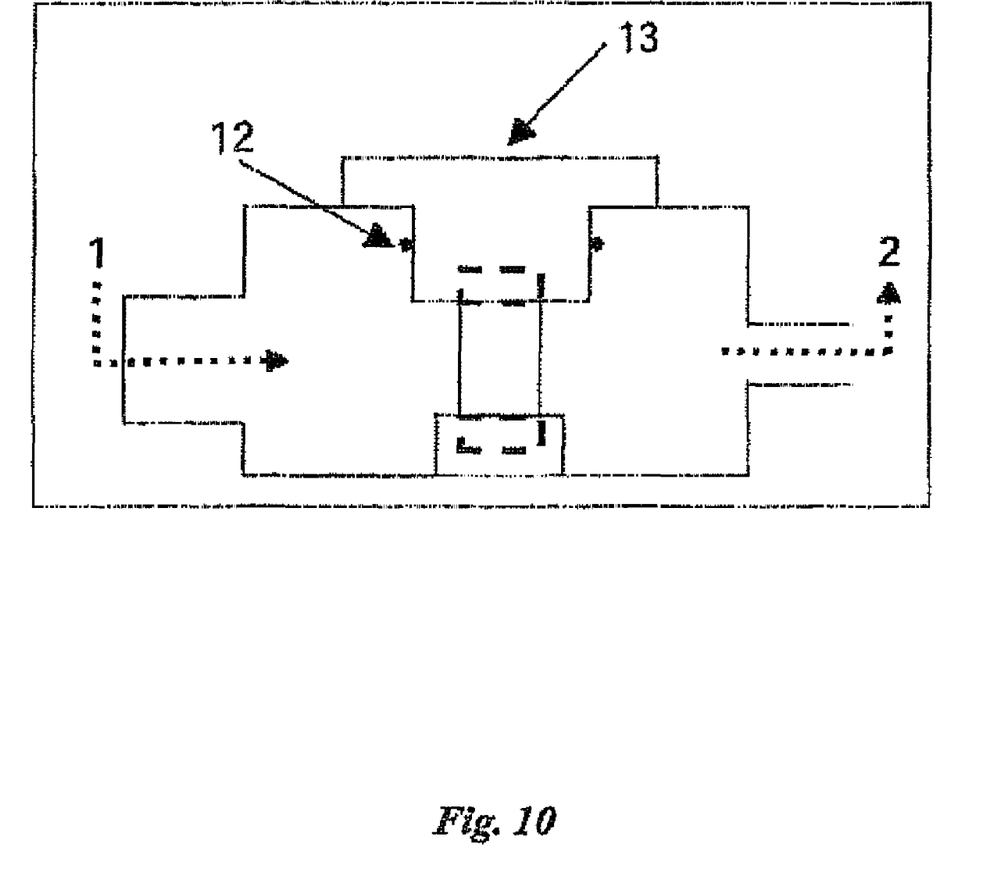
FIG. 10 corresponds to a transverse cross section of compartment (4) comprising a material according to the invention.

Use of the Material for the Non-Selective Detection of Formaldehyde and Acetaldehyde Measurements were carried out under conditions similar to those for Fluoral-P such as were described in Example 3. The aldehydes tested were formaldehyde and acetaldehyde. The curves represented in FIGS. 5 and 6 show the change in the absorbance over the course of the reaction of DNPH with formaldehyde. It is observed that the DNPH disappears rapidly in order to form a hydrazone whose spectrum is close to that of hydrazine. It was necessary to determine the differential absorbance (FIG. 6) in order to demonstrate the efficiency of the reaction.

The 2,4-dinitrophenylhydrazine (DNPH) reacts with most aldehydes by forming the corresponding hydrazone derivative. The material containing DNPH is non-selective and can therefore be used for a measurement of all of the aldehydes present in the air. Given the possibility of varying the pore size of the nanoporous material, it is possible to discriminate the aldehydes by their size in order to only detect small-size aldehydes (formaldehyde and acetaldehyde) It should be noted that small-size ketones (acetone) could interfere with this measurement.

The invention claimed is:

1. A method for detecting and/or assaying and/or trapping at least one aldehyde, comprising bringing a gas stream into contact with a solid and transparent material comprising a solid and transparent nanoporous metal oxide sol-gel matrix, said matrix containing at least one probe molecule bearing at least one reactive functional group which can react with an aldehyde functional group, said reactive functional group being selected from the group consisting of enaminones, β-diketone/amine pairs, and salts thereof.

2. The method as claimed in claim 1, characterized in that the aldehyde is chosen from formaldehyde, acetaldehyde, propionaldehyde, butyraldehyde, acrolein, pentanal, hexanal and benzaldehyde.

3. The method as claimed in claim 1, characterized in that it additionally comprises a step of directly analyzing the variation of the spectral properties of at least one probe molecule of the solid and transparent by at least one spectrophotometry technique.

4. The method as claimed in claim 1, characterized in that the enaminones correspond to the formula (I):

in which:
R₁ corresponds to a hydrogen, an alkyl or aryl radical;
R₂ corresponds to a hydrogen;
R₃ corresponds to a hydrogen, an alkyl or aryl radical;
R₄ corresponds to a hydrogen, an alkyl or aryl radical; and
R₅ corresponds to a hydrogen.

5. The method as claimed in claim 4, wherein $R_1$ and $R_3$ are independently a methyl, ethyl, isopropyl, butyl, isobutyl, tert-butyl, pentyl or phenyl radical and $R_4$ a hydrogen.

6. The method as claimed in claim 5, wherein $R_1$ is a methyl radical and $R_3$ a methyl or phenyl radical.

7. The method as claimed in claim 1, wherein the solid and transparent nanoporous metal oxide sol-gel matrix is produced from at least one metal oxide of formula (IV):

$$M(X)_m(OR_8)_n(R_9)_p$$

in which:
M corresponds to a metal chosen from silicon, aluminum, titanium, zirconium, niobium, vanadium, yttrium and cerium;
$R_8$ and $R_9$ correspond independently to an alkyl or aryl radical;
n, m and p are integers, such that their sum is equal to the valency of M and that n is greater than or equal to 2; and
X is a halogen.

8. The method as claimed in claim 7, characterized in that M is silicon or zirconium.

9. The method as claimed in claim 7, wherein $R_8$ and $R_9$ are independently methyl or ethyl radicals.

10. The method as claimed in claim 7, wherein X is chlorine.

11. The method as claimed in claim 9, wherein the metal oxide is $Si(OMe)_4$.

12. A solid and transparent material capable of reacting with at least one gaseous aldehyde, comprising a solid and transparent nanoporous metal oxide sol-gel matrix produced from at least one metal oxide of formula (IV):

$$M(X)_m(OR_8)_n(R_9)_p$$

in which:
M corresponds to a metal chosen from silicon, aluminum, titanium, zirconium, niobium, vanadium, yttrium and cerium;
$R_8$ and $R_9$ correspond independently to an alkyl or aryl radical;
n, m and p are integers, such that their sum is equal to the valency of M and that n is greater than or equal to 2; and
X is a halogen;
said solid and transparent matrix containing at least one probe molecule bearing at least one functional group that is reactive with an aldehyde functional group, said reactive functional group being selected from the group consisting of enaminones, β-diketone/amine pairs, and salts thereof.

13. The material as claimed in claim 12, wherein the radicals $R_8$ and $R_9$ of the metal oxide are independently methyl or ethyl radicals and that the probe molecule is an enaminone.

14. The material as claimed in claim 13, wherein the metal oxide is $Si(OMe)_4$ and the probe molecule is Fluoral-P.

15. The material as claimed in claim 12, wherein the at least one gaseous aldehyde comprises formaldehyde.

* * * * *